(12) United States Patent
Jung et al.

(10) Patent No.: US 11,104,044 B2
(45) Date of Patent: Aug. 31, 2021

(54) ROTATING ASSEMBLY AND APPARATUS FOR MANUFACTURING MICROSTRUCTURE COMPRISING SAME

(71) Applicant: JUVIC INC., Seoul (KR)

(72) Inventors: Hyung Il Jung, Seoul (KR); Hui Suk Yang, Seoul (KR)

(73) Assignee: JUVIC INC., Seoul (KR)

( * ) Notice: Subject to any disclaimer, the term of this patent is extended or adjusted under 35 U.S.C. 154(b) by 365 days.

(21) Appl. No.: 16/093,587

(22) PCT Filed: Apr. 12, 2017

(86) PCT No.: PCT/KR2017/003969
§ 371 (c)(1),
(2) Date: Oct. 12, 2018

(87) PCT Pub. No.: WO2017/179909
PCT Pub. Date: Oct. 19, 2017

(65) Prior Publication Data
US 2020/0230846 A1    Jul. 23, 2020

(30) Foreign Application Priority Data

Apr. 12, 2016 (KR) .................... 10-2016-0044918

(51) Int. Cl.
*B29C 41/50* (2006.01)
*B29C 41/04* (2006.01)

(52) U.S. Cl.
CPC ............ *B29C 41/045* (2013.01); *B29C 41/50* (2013.01)

(58) Field of Classification Search
CPC ....... B29C 41/04; B29C 41/045; B29C 41/06; B29C 41/50; B29C 64/241; B04C 7/08;
(Continued)

(56) References Cited

U.S. PATENT DOCUMENTS 1,876,261 A * 9/1932 Pemetzrieder ....... B22D 13/066
164/290
4,063,863 A * 12/1977 Hilmoe ................. B29C 39/42
425/425
(Continued)

FOREIGN PATENT DOCUMENTS

CN     105263561 A    1/2016
JP     2001-276665 A  10/2001
(Continued)

OTHER PUBLICATIONS

Office Action and Search Report of corresponding Chinese Patent Application No. 201780023330.4—8 pages (dated Jan. 3, 2020).
(Continued)

*Primary Examiner* — Joseph S Del Sole
*Assistant Examiner* — Margaret B Hayes
(74) *Attorney, Agent, or Firm* — Knobbe Martens Olson & Bear LLP

(57) ABSTRACT

Provided is a rotating assembly. The rotating assembly is for forming a microstructure, and comprises: a rotating body rotatable about a rotary shaft; a first support member installed on the rotating body so as to be spaced apart from the rotational shaft and having a predetermined viscous composition disposed on an outer surface thereof; and a fluid communicating portion for communicating the inside and the outside of the rotating body, wherein when the rotating body rotates, the viscous composition is pulled in a radially outward direction of the rotary shaft, and the pulled viscous composition is cured through the fluid communicating portion, thereby forming a microstructure.

20 Claims, 9 Drawing Sheets

(58) Field of Classification Search
CPC ......... B28B 21/30; B28B 21/80; B28B 23/10;
A23G 3/10; A23G 3/0051
USPC ................................................ 425/8, 9, 425
See application file for complete search history.

(56) References Cited

U.S. PATENT DOCUMENTS

| | | | |
|---|---|---|---|
| 4,167,381 A * | 9/1979 | Hilmoe ................. | B29C 33/306 |
| | | | 164/289 |
| 9,944,019 B2 * | 4/2018 | Falo, Jr. ............... | A61K 9/0021 |
| 2008/0031987 A1 * | 2/2008 | Huang ................. | A23G 3/0025 |
| | | | 425/8 |
| 2016/0067469 A1 | 3/2016 | Jung et al. | |

FOREIGN PATENT DOCUMENTS

| | | | |
|---|---|---|---|
| JP | 2009-195583 A | 9/2009 |
| JP | 2012-513889 A | 6/2012 |
| JP | 2014-511443 A | 4/2013 |
| JP | 2015-009211 A | 1/2015 |
| KR | 10-2014-0131879 A | 11/2014 |

OTHER PUBLICATIONS

Office Action of corresponding Japanese Patent Application No. 2018-554071—5 pages (dated Jul. 17, 2019).
International Search Report of corresponding Patent Application No. PCT/KR2017/003969—4 pages (dated Aug. 16, 2017).

\* cited by examiner

ROTATING ASSEMBLY AND APPARATUS FOR MANUFACTURING MICROSTRUCTURE COMPRISING SAME

TECHNICAL FIELD

The present invention relates to a rotation assembly and an apparatus for fabricating a micro structure including the same.

BACKGROUND ART

Many medications and medicines for the treatment of disease have been developed, but a biological barrier (e.g., the skin, arteria buccalis and a blood brain barrier) penetration problem and an efficiency problem of medication transfer when medication is delivered to the body still remain unsolved.

In general, medication is orally administrated as an antibiotic tablet or a capsule tablet, but many medications cannot be effectively delivered through such an administration method because they are digested or absorbed in a gastrointestinal tract or lost by the mechanism of the liver. Moreover, some medications cannot be effectively spread through the mucous membrane of an intestine. Furthermore, the compliance of a patient is also a problem (e.g., in the case of a critical patient who must take medication at a specific interval or who cannot take drugs).

Another common technology is to use a conventional needle in medication transfer. This method is more effective than oral administration. In contrast, there are problems in that an accompanied pain and local damage to the skin in a needle portion, bleeding, and disease infection in a needle portion are caused.

In order to solve such problems, several micro structures including a microneedle have been developed. Microneedles developed so far have been chiefly used for medication transfer within a living body, blood-gathering, and the detection of an analysis substance within the body.

However, a conventional method of fabricating a micro structure using a mold is the most common fabrication method, but the fabrication method using a mold has a critical point in that a loss occurs in a separation process from a mold.

DISCLOSURE

Technical Problem

An embodiment of the present invention is to provide a rotation assembly, which can induce solidification simultaneously with the molding of a viscous composition through rotation without a separate mold through a viscous composition and control medication while protecting the medication in various conditions because a separate annealing process or separation and fixing are not used, and an apparatus for fabricating a micro structure including the same.

Furthermore, an embodiment of the present invention is to provide a rotation assembly, which can fabricate a micro structure having a diameter of a micro unit and a sufficient effective length and hardness, and an apparatus for fabricating a micro structure including the same.

An embodiment of the present invention is to provide a rotation assembly, which can selectively exclude a process that may break the activation of medication or a beauty ingredient, such as high temperature processing and organic solvent processing, reduce damage attributable to contact and separation, and overcome the limitation of an aspect ratio of a fabricated micro structure using a centrifugal force, and an apparatus for fabricating a micro structure including the same.

Furthermore, an embodiment of the present invention is to provide a rotation assembly, which can increase a yield through loading and can be simply fabricated/assembled unlike in the existing complicated mold fabrication process, and an apparatus for fabricating a micro structure including the same.

Technical Solution

In accordance with an aspect of the present invention, there is provided a rotation assembly for forming a micro structure, including a rotation body rotatable around a rotation shaft; a first support member positioned in the rotation body in such a way as to be isolated from the rotation shaft, a given viscous composition being positioned on an outer surface of the first support member; and a fluid communication unit through which an inside and outside of the rotation body communicate with each other, wherein when the rotation body is rotated, the viscous composition is outward extended in a radial direction of the rotation shaft, and the extended viscous composition is hardened through the fluid communication unit to form a micro structure.

In this case, a second support member having an inner surface facing the outer surface of the first support member and spaced apart from the first support member in the radial direction of the rotation shaft is further included. When the rotation body is rotated, the viscous composition may be extended up to the inner surface of the second support member to form a micro structure.

In this case, the fluid communication unit may include a flow hole formed in the outer circumference surface of the rotation body.

In this case, an accommodation groove communicating with the flow hole may be formed in the rotation body, and at least the first support member of the first support member and the second support member may be positioned in the accommodation groove.

In this case, a fixing member fixing the first support member and the second support member to the accommodation groove is further included. A cross section of the fixing member may be formed to correspond to a cross section of the accommodation groove so that the fixing member is inserted into the accommodation groove.

In this case, a coupling groove outward depressed in the radial direction may be formed on one side of the fixing member, and the first support member and the second support member may be coupled to the inner surface of the coupling groove.

In this case, the fixing member may include guidance members protruded toward one side of the rotation body on both end sides of the one side to guide the fixing member when the fixing member is inserted into the accommodation groove.

In this case, the fixing member may further include a fastening member fixing the fixing member to the accommodation groove, the fastening member may be a bolt, a through hole through which the bolt penetrates may be formed in the fixing member, and a coupling hole to which the bolt is coupled may be formed in the outer circumference surface of the rotation body.

In this case, the fixing member may have a cross section of "a ⊂-letter" form.

In this case, an interval maintenance member for maintaining an interval between the first support member and the support member may be further included between the first support member and the second support member.

In this case, the interval maintenance member may include an interval frame of a ⊂-letter shape having one side come into contact with the first support member and the other side come into contact with the second support member.

In this case, the interval frame may be a holder member having a fixing groove formed in one surface in order to fix the first support member and having the end of the fixing groove come into contact with another surface of the second support member.

In this case, the first support member and the second support member may be formed in a plural number, the coupling groove may include a plurality of coupling members arranged in parallel from one side within the coupling groove toward an end of the coupling groove, and the plurality of first support members and the plurality of second support members may be disposed in the plurality of coupling members.

In this case, each of the plurality of coupling members may be formed in a sheet form, and a protrusion member may be protruded from one side of each of the plurality of coupling members to maintain an interval between the plurality of coupling members.

In this case, the accommodation groove may be formed in a plural number in the radial direction of the rotation body, and at least one of the first support member and the second support member may be positioned in each of the plurality of accommodation grooves.

In this case, the first support member and the second support member may be formed in a sheet or curve form.

In this case, the viscous composition may be selected from a group consisting of hyaluronic acid and salt thereof, polyvinylpyrrolidone, cellulose polymer, dextran, gelatine, glycerine, polyethylene glycol, polysorbate, propylene glycol, povidone, carbomer, gum ghatti, guar gum, glucomannan, glucosamine, dammer resin, rennet casein, locust bean gum, microfibrillated cellulose, psyllium seed gum, xanthan gum, arabino galactan, arabic gum, alginic acid, gelatine, gellan gum, carrageenan, karaya gum, curdlan, keto acid, chitin, taragum, tamarind gum, tragacanth gum, furcelleran, pectin and pullulan, polystyrene, polymer.

In this case, after the rotation body is rotated, the first support member and the second support member may be rotated to change their positions and are then rotated.

In accordance with another aspect of the present invention, there is provided an apparatus for fabricating a micro structure, including a housing in which a hollow portion is formed; a rotation assembly according to any one of claims 1 to 18, wherein the rotation assembly is formed within the housing to rotate around a rotation shaft; and a pressure reduction unit reducing pressure of the hollow portion.

In this case, a housing cover coupled to the housing to open or close an opening part formed on one side of the hollow portion may be further included.

In this case, the pressure reduction unit may form a vacuum in the hollow portion.

In this case, a temperature and magnetic field of the hollow portion may be adjustable.

Advantageous Effects

The rotation assembly and the apparatus for fabricating a micro structure including the same according to embodiments of the present invention can fabricate a micro structure having a diameter of a micro unit and a sufficient effective length and hardness through a viscous composition using a centrifugal force.

The rotation assembly and the apparatus for fabricating a micro structure including the same according to embodiments of the present invention can selectively exclude a process that may break the activation of medication or a beauty ingredient, such as high temperature processing and organic solvent processing, reduce damage attributable to contact and separation, and overcome the limitation of an aspect ratio of a fabricated micro structure using a centrifugal force.

The rotation assembly and the apparatus for fabricating a micro structure including the same according to embodiments of the present invention can secure rotation stability and safety and prevent the occurrence of heat attributable to air frication by minimizing air resistance when the first support member and the second support member are rotated because the first support member and the second support member are disposed within the rotation body.

The rotation assembly and the apparatus for fabricating a micro structure including the same according to embodiments of the present invention can adjust the time taken for a viscous composition G to be hardened based on the amount of an inflow or outflow fluid when the viscous composition is hardened because the flow hole is included.

The rotation assembly according to an embodiment of the present invention can prevent the first support member and the second support member from breaking away when they are rotated because it includes the cover member, can fabricate a precise and uniform micro structure by adjusting the time taken for a viscous composition to be hardened through control of the amount of an inflow fluid, and can diversify the concentration of a viscous composition.

In the rotation assembly according to an embodiment of the present invention, the first support member and the second support member can be easily inserted and positioned because the handle groove is formed in the fixing member.

The rotation assembly according to an embodiment of the present invention includes the guidance member, and thus can guide the fixing member when the fixing member is inserted into the accommodation groove.

The rotation assembly according to an embodiment of the present invention includes the interval maintenance member to maintain the interval between the first support member and the second support member. Accordingly, a viscous composition positioned on the outer surface of the first support member can be extended up to the inner surface of the second support member when the rotation body is rotated, thereby forming a micro structure.

The rotation assembly and the apparatus for fabricating a micro structure including the same according to embodiments of the present invention can adjust a shape or strength of a micro structure by diversifying a cutting direction when a viscous composition extended to the second support member is cut because the holder member is included and the first support member and the second support member are spaced apart.

The rotation assembly and the apparatus for fabricating a micro structure including the same according to embodiments of the present invention can increase the yield of a micro structure in a single process because the plurality of coupling members is included.

BEST MODE FOR INVENTION

Figure 1:
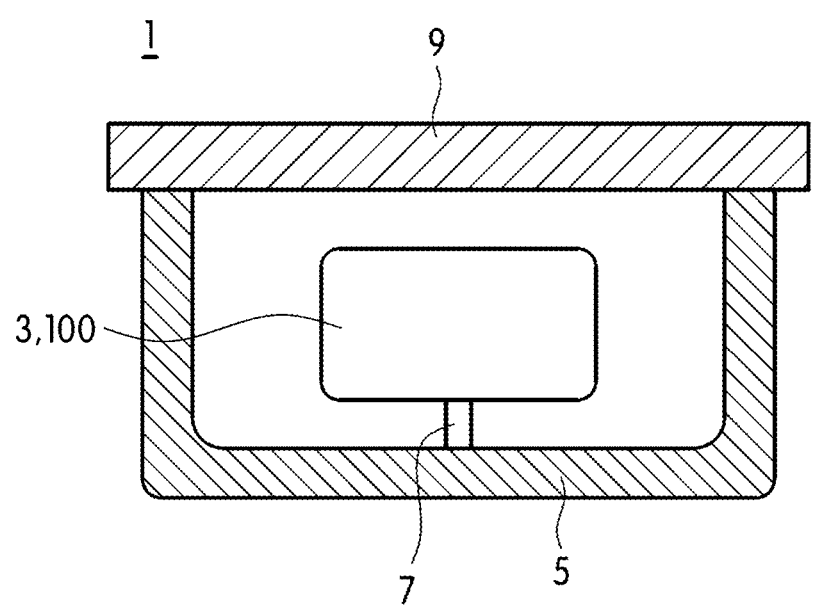
FIG. 1 is a schematic diagram showing an apparatus for fabricating a micro structure including a rotation assembly according to an embodiment of the present invention.

Hereinafter, embodiments of the present invention are described in detail with reference to the accompanying drawings so that a person having ordinary skill in the art to which the present invention pertains may easily practice the embodiments. However, the present invention may be implemented in various different forms and is not limited to the embodiments described herein. Furthermore, in the drawings, in order to clarify a description of the present invention, parts not related to the description are omitted, and the same reference numbers are used to refer to the same or similar parts throughout the specification.

In this specification, it is to be understood that a term, such as "include" or "have", is intended to designate that a characteristic, number, step, operation, element, part or a combination of them described in the specification is present, and does not exclude the presence or addition possibility of one or more other characteristics, numbers, steps, operations, elements, parts, or combinations of them in advance. Furthermore, when it is described that one part, such as a layer, film, area, or plate, is "over" or "on" the other part, the one part may be "directly" on the other part or a third part may be present between the two parts. In contrast, when it is described that one part is "directly on" the other part, it means that a third part is not present between the two parts.

FIG. 1 is a schematic diagram showing an apparatus for fabricating a micro structure including a rotation assembly according to an embodiment of the present invention.

Referring to FIG. 1, the apparatus 1 for fabricating a micro structure including a rotation assembly 3 according to an embodiment of the present invention may include a housing 5, the rotation assembly 3 and a housing cover 9. Accordingly, the apparatus 1 for fabricating a micro structure including the rotation assembly 3 according to an embodiment of the present invention can easily fabricate a micro structure (not shown) by rotating the rotation assembly to induce the tension of a viscous composition. In this case, the fabricated micro structure may have a diameter of a micro unit and a sufficient effective length and hardness, and can overcome the limitation of an aspect ratio.

Referring to FIG. 1, in an embodiment of the present invention, a hollow portion may be formed within the housing 5. A rotation shaft member 7 may be formed at the central part of the hollow portion. In this case, the rotation assembly 3 may be coupled to the rotation shaft member 7 and rotated therewith within the housing.

Furthermore, an opening part (not shown) may be formed on one side of the hollow portion of the housing 5, for example, at the top of the housing as shown in FIG. 1. In this case, the opening part may be open and close through the housing cover 9.

The time taken for a viscous composition G to be hardened can be reduced by rotating the rotation assembly in the state in which the inside of the housing has been a vacuum state when the rotation assembly 3 according to an embodiment of the present invention is rotated within the housing 5. Furthermore, when the rotation assembly 3 is rotated at high speed, air resistance is reduced. Accordingly, rotation stability and safety can be secured, and the occurrence of heat attributable to air frication can be prevented.

When the inside of the housing is a vacuum, the hardening time can be adjusted because a viscous composition positioned within the rotation assembly is smoothly evaporated.

The inside of the housing does not need to be essentially a vacuum. The effect can be achieved only when pressure within the housing is smaller than pressure within the rotation assembly. Furthermore, if a viscous composition is hardened by reducing pressure within the housing, a more uniform micro structure can be fabricated compared to hardening using a flow.

Furthermore, air resistance when the rotation assembly 3 is rotated at high speed can be reduced by adjusting a temperature and magnetic field within the housing. Accordingly, rotation stability and safety can be secured and the occurrence of heat attributable to air frication can be prevented.

Figure 2:
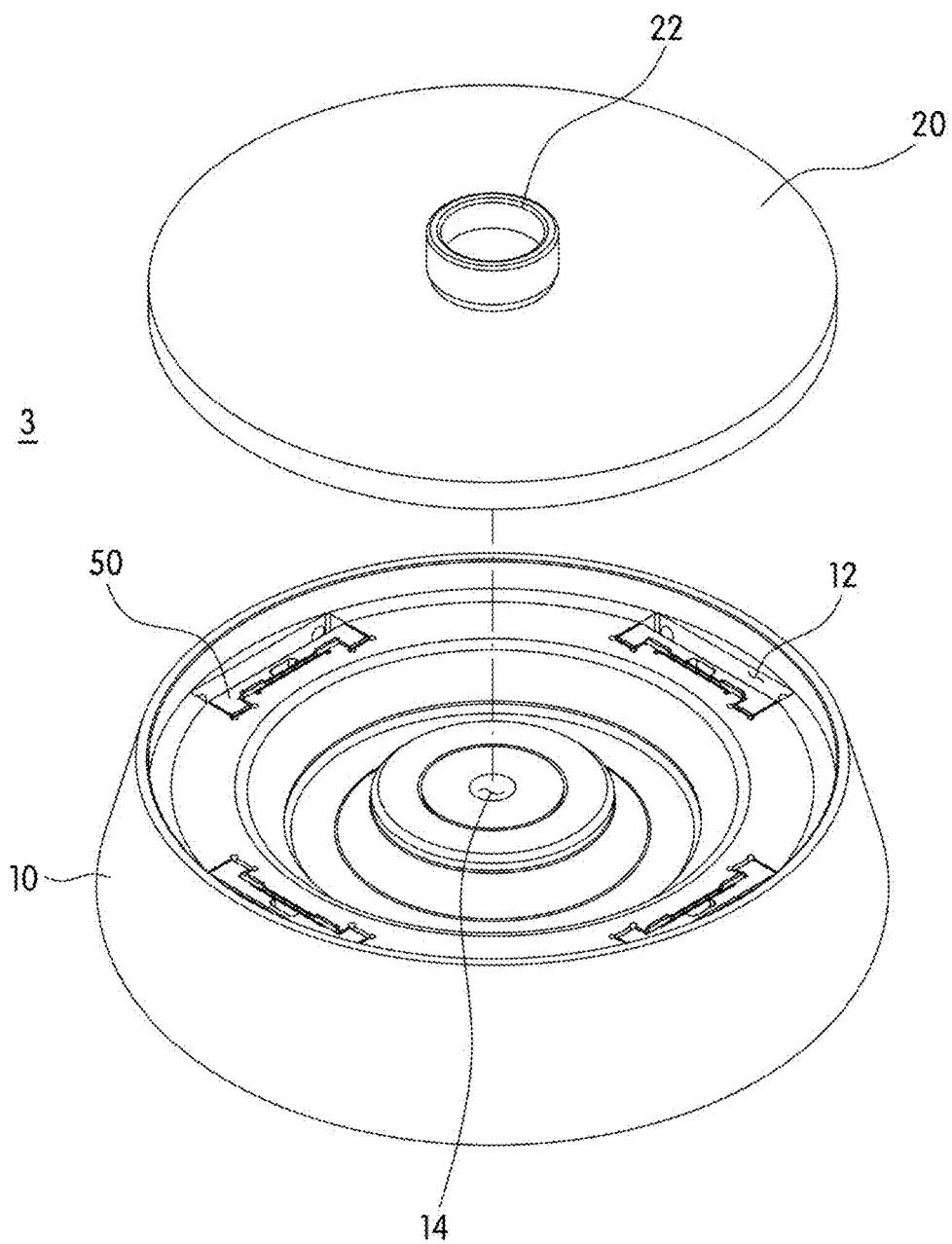
FIG. 2 is a perspective view showing a rotation assembly according to an embodiment of the present invention.
Figure 3:
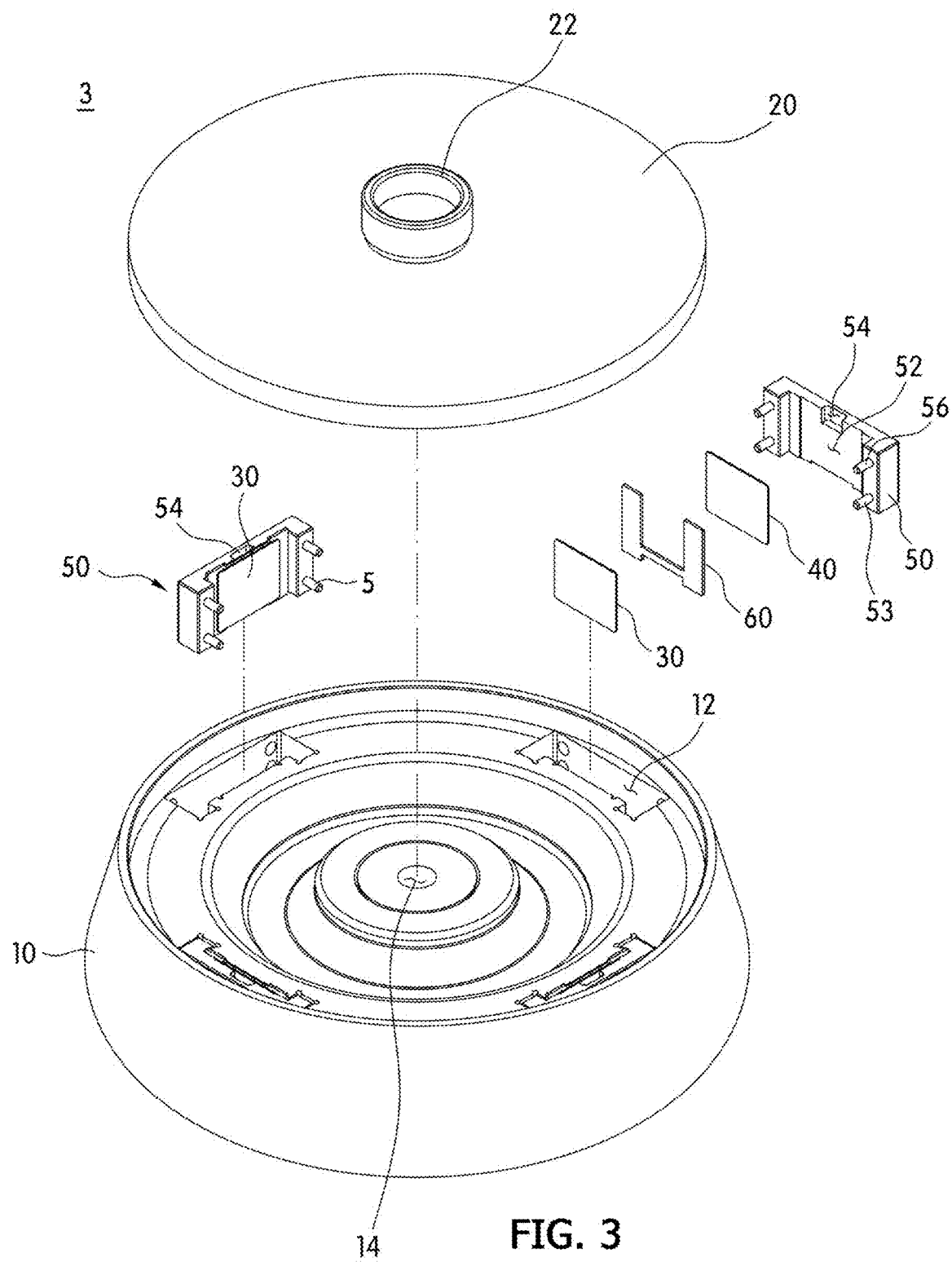
FIG. 3 is an exploded perspective view showing a rotation assembly according to an embodiment of the present invention.
Figure 4:
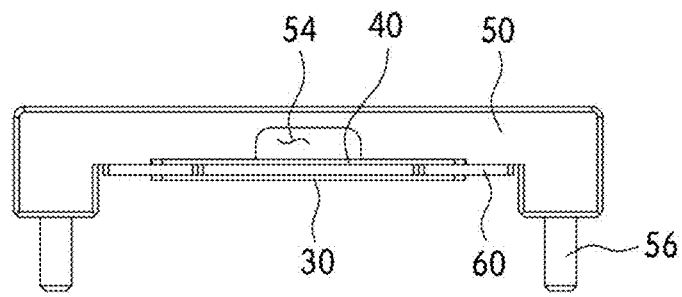
FIG. 4 is a plan view showing the fixing member of the rotation assembly according to an embodiment of the present invention.

FIG. 2 is a perspective view showing a rotation assembly according to an embodiment of the present invention. FIG. 3 is an exploded perspective view showing a rotation assembly according to an embodiment of the present invention. FIG. 4 is a plan view showing the fixing member of the rotation assembly according to an embodiment of the present invention.

Referring to FIG. 2, the rotation assembly 3 according to an embodiment of the present invention may include a rotation body 10, a first support member 30 and a second support member 40.

In an embodiment of the present invention, the rotation body 10 is a cylindrical form, and a center hole (not shown) may be formed in the rotation body 10 so that the rotation shaft member 7 is coupled to the central part and rotated therewith. The rotation body 10 may rotate around a rotation shaft formed on the extension line of the rotation shaft member 7.

Referring to FIG. 3, in an embodiment of the present invention, accommodation grooves 12 of a "⊂-letter" form may be formed in the rotation body 10. In this case, the accommodation grooves 12 may be formed on the upper side of the rotation body 10.

Furthermore, the first support member 30 and the second support member 40 are disposed in the accommodation groove 12 of the rotation body 10, and can minimize air resistance when the first support member and the second support member are rotated. That is, air resistance is minimized when the first support member 30 and the second support member 40 are disposed in the rotation body 10 and rotated, thereby being capable of securing rotation stability and safety and preventing the occurrence of heat attributable to air frication.

In an embodiment of the present invention, as shown in FIG. 3, four accommodation grooves 12 may be spaced apart and disposed in the circumference direction of the rotation body 10, but are not limited thereto. A plurality of accommodation grooves may be formed if the weight balance of the rotation body 10 can be adjusted.

The rotation assembly according to an embodiment of the present invention may include a fluid communication unit through which the inside and outside of the rotation assembly communicate with each other. The fluid communication unit may have a pipe member, a flow hole or a construction capable of a fluid flow between the inside and outside of the rotation assembly, such as an isolated space between the rotation body and the cover member.

For example, the fluid communication unit may include a flow hole formed in the outer circumference surface of the rotation body 10. The flow hole may be formed in a plural number. The plurality of flow holes may be disposed in parallel on the outer circumference surface of the rotation body.

The rotation assembly 3 according to an embodiment of the present invention includes the fluid communication unit, and thus can adjust the time taken for a viscous composition to be hardened depending on the amount of a fluid introduced into or discharged from the accommodation grooves 12 through the fluid communication unit when a viscous composition G is hardened.

Furthermore, a viscous composition evaporated through the fluid communication unit can be discharged to the outside of the rotation assembly. Accordingly, a viscous composition can be hardened to fabricate a micro structure.

Referring to FIGS. 2 and 3, in an embodiment of the present invention, the first support member 30 may be formed in the accommodation groove 12 of the rotation body 10 in such a way as to be isolated from the rotation shaft. In this case, a given viscous composition G may be positioned on the outer surface of the first support member 30.

In an embodiment of the present invention, the second support member 40 may be spaced apart from the first support member 30 in the radial direction of the rotation shaft. In this case, the second support member 40 may have an inner surface facing the outer surface of the first support member 30. Furthermore, in an embodiment of the present invention, the first support member 30 and the second support member 40 may have a rectangle, circle or semi-circle sheet form. Furthermore, the first support member 30 and the second support member 40 may have a curved surface form, but is not limited thereto.

In the rotation assembly 3 according to an embodiment of the present invention, when the rotation body 10 is rotated, a viscous composition positioned on the outer surface of the first support member 30 is extended up to the inner surface of the second support member 40 outward in the radial direction of the rotation shaft, thereby being capable forming a micro structure.

Accordingly, the rotation assembly 3 according to an embodiment of the present invention can fabricate a micro structure having a diameter of a micro unit and a sufficient effective length and hardness through a viscous composition using a centrifugal force.

Furthermore, the rotation assembly 3 according to an embodiment of the present invention can exclude a process that may break the activation of medication or a beauty ingredient, such as high temperature processing or organic solvent processing, can reduce damage attributable to contact and separation, and can overcome the limitation of an aspect ratio of a fabricated micro structure.

Referring to FIGS. 2 and 3, in an embodiment of the present invention, a cover member 20 may be included so that the accommodation grooves 12 of the rotation body 10 are open and closed. In this case, the cover member 20 may have a disc form. A coupling bolt 22 may be coupled to the central part of the cover member 20.

In an embodiment of the present invention, the coupling bolt 22 may be coupled to a screw hole 14 formed on the extension line of the rotation shaft of the rotation body 10, thereby opening or closing the accommodation grooves 12. Accordingly, the rotation assembly 3 according to an embodiment of the present invention includes the cover member 20 and thus can prevent the first support member 30 and the second support member 40 from breaking away when they are rotated.

Furthermore, the rotation assembly 3 according to an embodiment of the present invention includes the cover member 20, and can thus adjust the time taken for a viscous composition to be hardened by adjusting the amount of a fluid introduced into the accommodate grooves 12 through the cover member when the viscous composition is hardened.

Referring to FIGS. 3 and 4, the rotation assembly 3 according to an embodiment of the present invention includes a fixing member 50, and can thus fix the first support member 30 and the second support member 40 to the accommodation groove 12.

In this case, a cross section of the fixing member 50 may be formed to correspond to a cross section of the accommodation groove so that the fixing member is inserted into the accommodation groove 12. Accordingly, in an embodiment of the present invention, the cross section of the fixing member 50 may have a E-letter shape, but is not limited thereto.

In an embodiment of the present invention, a coupling groove 52 outward depressed in the radial direction may be formed on one side of the fixing member 50, for example, the inner surface of the fixing member as shown in FIG. 3. Furthermore, in an embodiment of the present invention, the first support member 30 and the second support member 40 may be coupled to the inner surface of the coupling groove 52.

Referring to FIG. 3, a handle groove 54 is formed at the top of the coupling groove 52 of the fixing member 50, so the first support member 30 and the second support member 40 can be easily inserted and positioned. In this case, the handle groove 54 may be formed in a L-letter shape in the inner surface of the coupling groove 52 and the top of the fixing member 50.

In an embodiment of the present invention, the fixing member 50 may include guidance members 56 on both end sides thereof. In this case, the guidance members 56 may be formed on one side of the fixing member 50, for example, on both end sides of the inner surface of the fixing member as shown in FIG. 3, and may be protruded toward the inside of the rotation body 10.

Accordingly, the rotation assembly 3 according to an embodiment of the present invention includes the guidance members 56, and thus can guide the fixing member 50 when the fixing member 50 is inserted into the accommodation groove 12.

Referring to FIG. 3, in an embodiment of the present invention, the fixing member 50 may further include a fastening member (not shown) for fixing the fixing member to the accommodation groove 12. In this case, the fastening member may be a bolt, but is not limited thereto.

In an embodiment of the present invention, through holes 58 may be formed on both end sides of the fixing member 50 so that bolts can pass through the through holes. Furthermore, coupling holes (not shown) to which the bolts can be coupled may be formed at both ends of the inner surface of the fixing member.

Accordingly, in an embodiment of the present invention, the bolt is inserted into the coupling hole formed in the rotation body 10 and the through hole (not shown) formed in the fixing member 50, so the fixing member can be coupled to the accommodation groove 12 of the rotation body.

Referring to FIG. 3, the rotation assembly 3 according to an embodiment of the present invention includes an interval maintenance member 60 to maintain the interval between the first support member 30 and the second support member 40. Accordingly, when the rotation body 10 is rotated, a viscous composition positioned on the outer surface of the first support member can be extended up to the inner surface of the second support member 40, thereby forming a micro structure.

Referring to FIGS. 3 and 4, in an embodiment of the present invention, the interval maintenance member 60 may be positioned between the first support member 30 and the second support member 40. In this case, one side of the interval maintenance member 60, for example, the inner surface of the interval maintenance member may come into contact with the first support member 30 and the other side of the interval maintenance member 60, for example, the outer surface of the interval maintenance member may come into contact with the second support member 40, as shown in FIG. 3.

Furthermore, in an embodiment of the present invention, the interval maintenance member may have a cross section of a ⊂-letter shape, and may be an interval frame 60. In this case, the first support member 30 and the second support member 40 may be spaced apart by the thickness of the interval frame 60.

Figure 5:
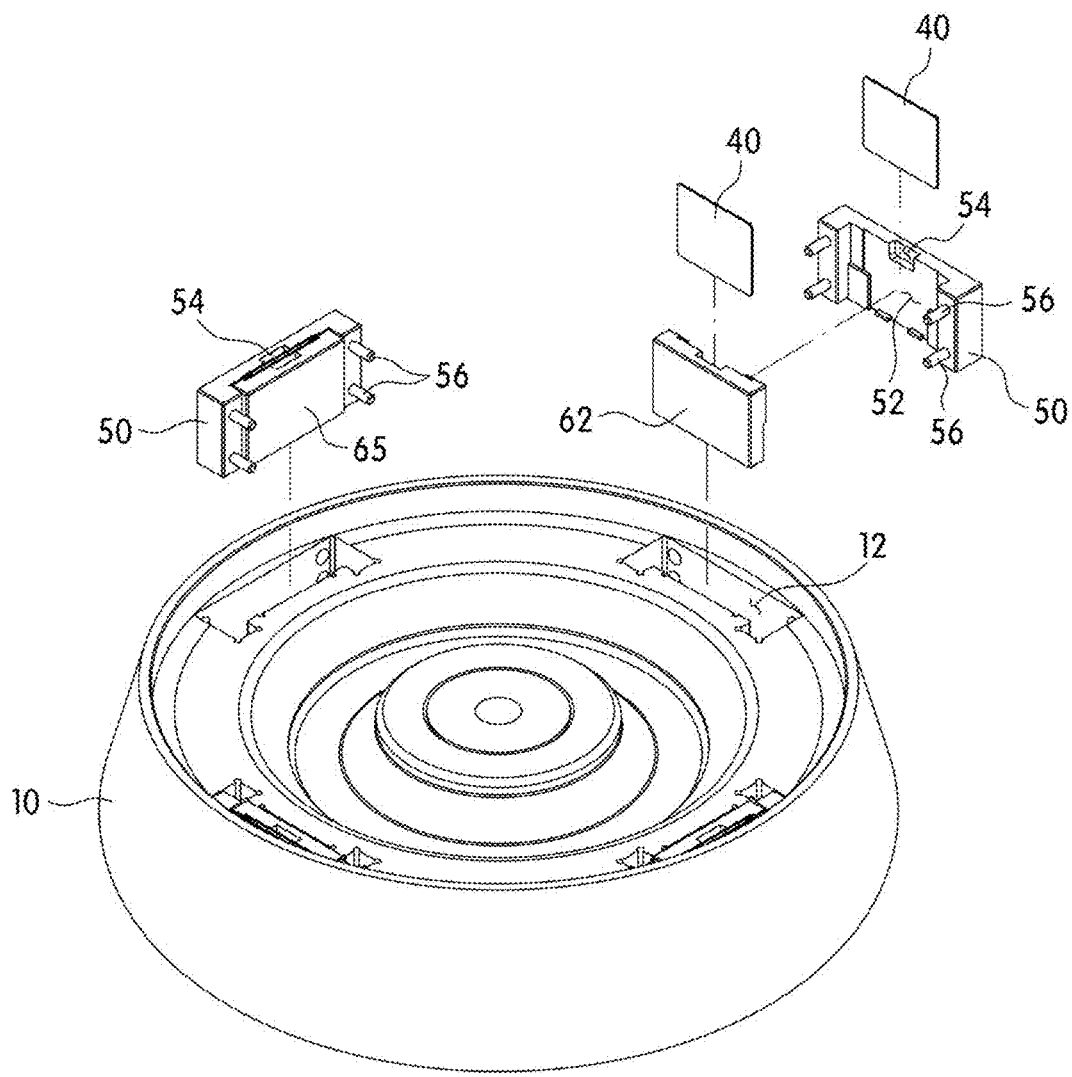
FIG. 5 is an exploded perspective view showing a first modification example of a rotation assembly according to an embodiment of the present invention.
Figure 6:
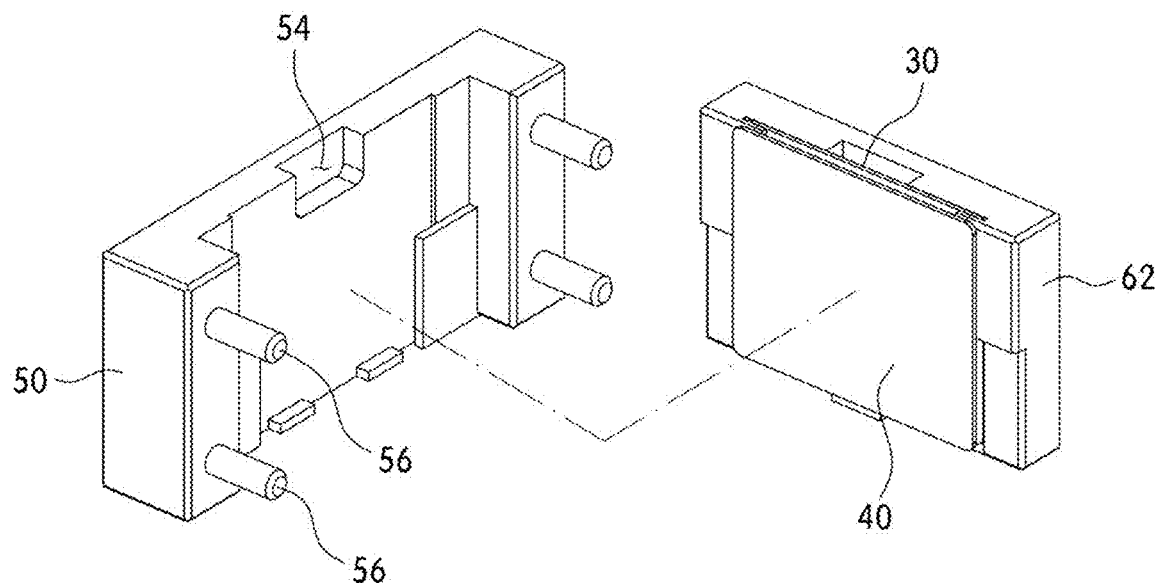
FIG. 6 is an exploded perspective view showing a first modification example of the fixing member of the rotation assembly according to an embodiment of the present invention.
Figure 7:
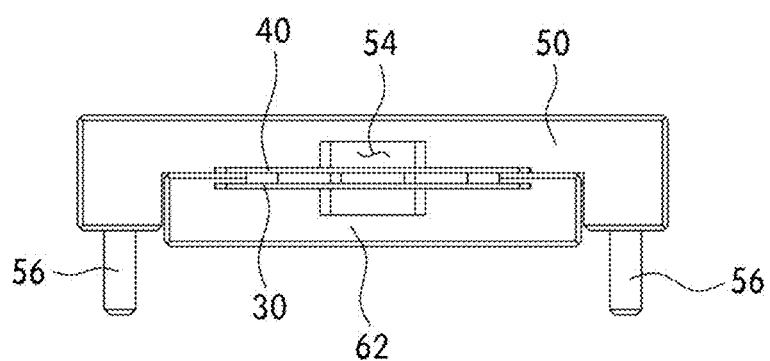
FIG. 7 is a plan view showing the first modification example of the fixing member of the rotation assembly according to an embodiment of the present invention.

FIG. 5 is an exploded perspective view showing a first modification example of a rotation assembly according to an embodiment of the present invention. FIG. 6 is an exploded perspective view showing a first modification example of the fixing member of the rotation assembly according to an embodiment of the present invention. FIG. 7 is a plan view showing the first modification example of the fixing member of the rotation assembly according to an embodiment of the present invention.

Referring to FIG. 5, in an embodiment of the present invention, an interval maintenance member may be a holder member 62. In this case, a fixing groove (not shown) may be formed on one side of the holder member 62, for example, the outer surface of the holder member as shown in FIGS. 5 and 6.

Furthermore, in an embodiment of the present invention, the holder member 62 has a cross section of a ⊂-letter shape. The other side of the second support member 40, for example, the outer surface of the second support member may come into contact with the end of the fixing groove as shown in FIG. 5.

In this case, referring to FIG. 6, in an embodiment of the present invention, insertion grooves (not shown) of a circular section may be formed at both sides of the holder member 62. In this case, a pin member (not shown) formed in the coupling groove 52 of the fixing member 50 is inserted and coupled to the insertion groove, so the holder member 62 can be coupled to the fixing member.

Referring to FIG. 6, in an embodiment of the present invention, the first support member 30 is coupled to the fixing groove of the holder member 62, and the second support member 40 comes into contact with both ends of the holder member 62 to maintain the interval between the first support member and the second support member. Accordingly, when the rotation body 10 is rotated, a viscous composition positioned on the outer surface of the first support member can be extended up to the inner surface of the second support member 40, thereby forming a micro structure.

Furthermore, in an embodiment of the present invention, the first support member 30 is coupled to the holder member 62 and the second support member 40 is coupled to the fixing member 50 so that the first support member and the second support member are separately separated. Accordingly, a loss occurring in a cutting process when a viscous composition extended to the second support member is cut and the limitation of fabrication yield can be overcome.

Figure 8:
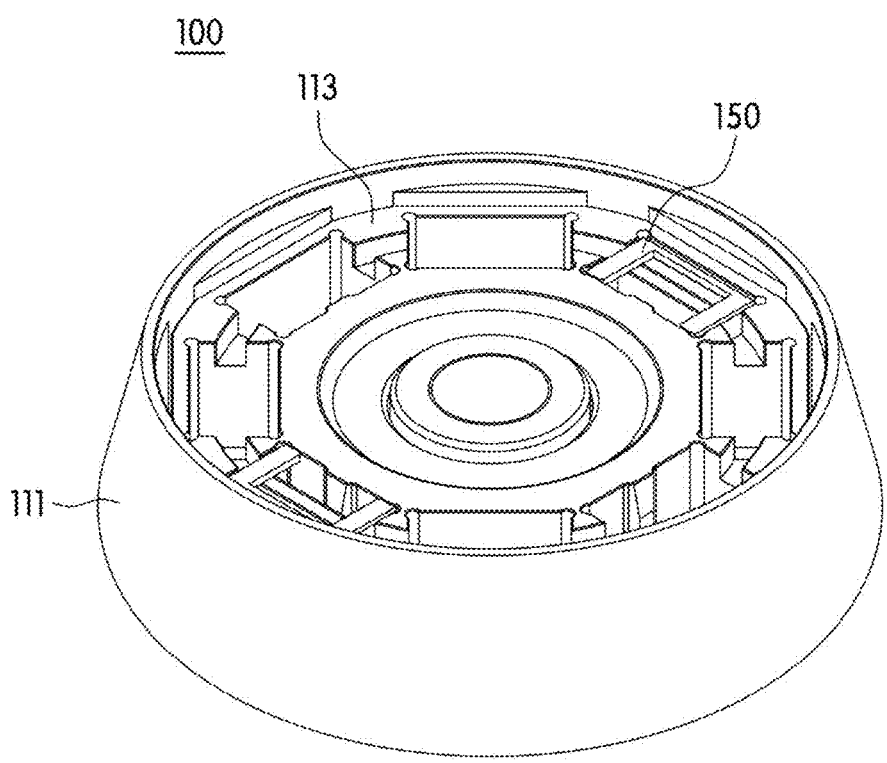
FIG. 8 is a perspective view showing a second modification example of a rotation assembly according to an embodiment of the present invention.
Figure 9:
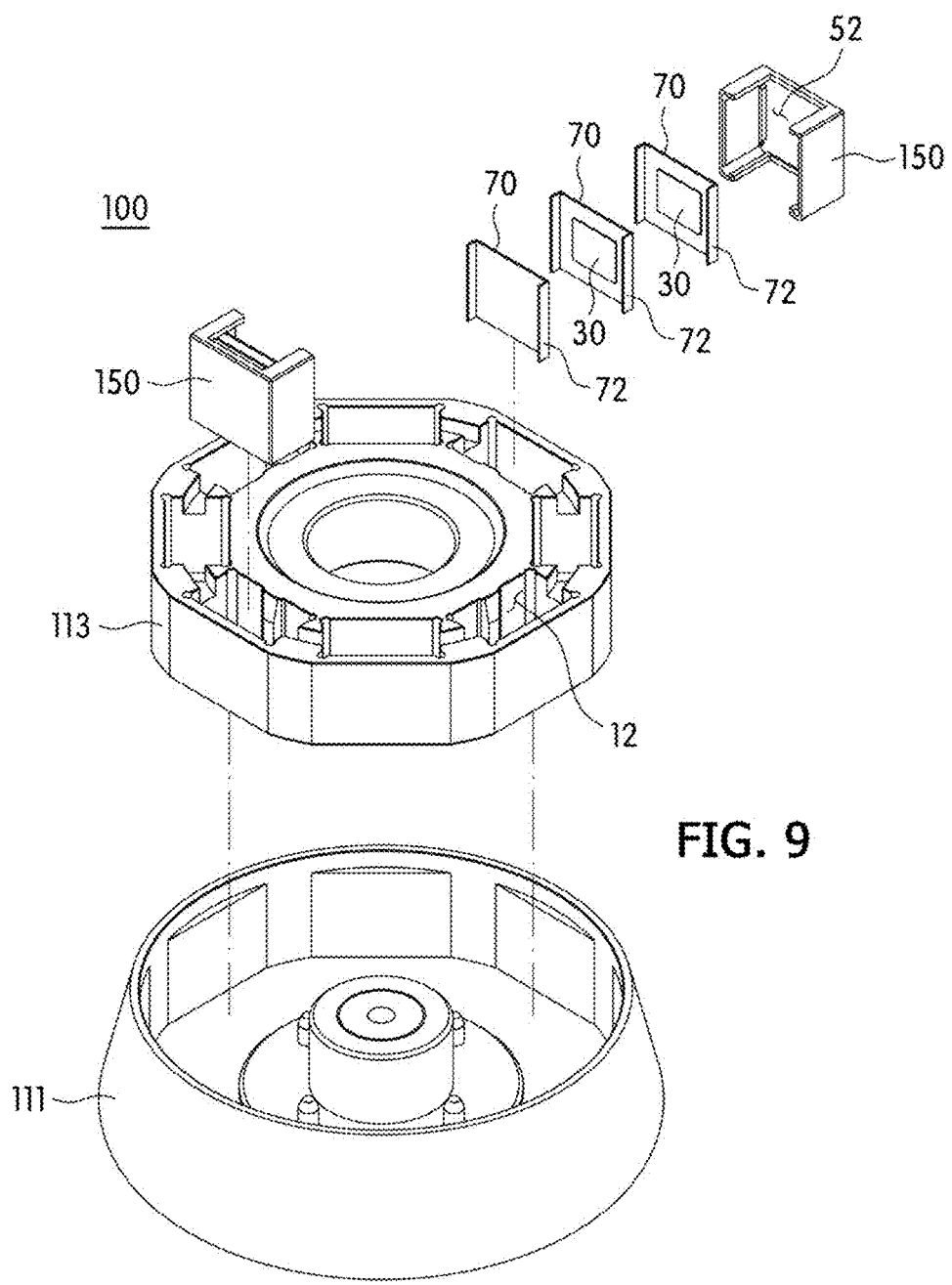
FIG. 9 is an exploded perspective view showing the second modification example of the rotation assembly according to an embodiment of the present invention.
Figure 10:
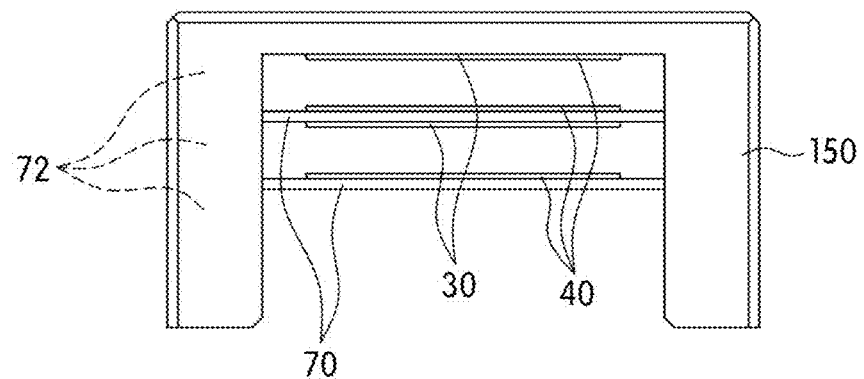
FIG. 10 is a plan view showing a second modification example of the fixing member of the rotation assembly according to an embodiment of the present invention.

FIG. 8 is a perspective view showing a second modification example of a rotation assembly according to an embodiment of the present invention. FIG. 9 is an exploded perspective view showing the second modification example of the rotation assembly according to an embodiment of the present invention. FIG. 10 is a plan view showing a second modification example of the fixing member of the rotation assembly according to an embodiment of the present invention.

Referring to FIGS. 8 and 9, in an embodiment of the present invention, a plurality of coupling members 70 may be arranged in parallel from the inner surface of the coupling groove toward the end of the coupling groove in the coupling groove 52 of a fixing member 150.

In this case, in an embodiment of the present invention, the rotation assembly may include a fluid communication unit. In this case, the rotation assembly may be rotated without the cover member 20 in order for a viscous composition within the rotation assembly to communicate with the outside of the rotation assembly.

Referring to FIG. 9, in an embodiment of the present invention, the first support member 30 and the second support member 40 may be formed in a plural number. The plurality of first support members 30 and the plurality of second support members 40 are disposed in the plurality of coupling members 71. Accordingly, the yield of a micro structure in a single process can be increased.

In an embodiment of the present invention, each of the plurality of coupling members 70 may be formed in a sheet form. A protrusion member 72 may be positioned between the plurality of coupling members. In this case, a pair of the protrusion members 72 may be formed on both end sides of the coupling member 70 and protruded toward the inside in a radial direction.

Referring to FIG. 10, a rotation assembly 100 according to an embodiment of the present invention includes the protrusion members 72 to maintain the interval between the plurality of coupling members 70, thereby being capable of maintaining the interval between the first support member 30 and the second support member 40.

Referring to FIGS. 9 and 10, in an embodiment of the present invention, the coupling member 70 and a pair of the protrusion members 72 formed on both end sides of the coupling member may be integrated, but are not limited thereto.

Referring to FIGS. 8 and 9, a rotation body 110 may include an outside body 111 and an inside body 113. In an embodiment of the present invention, a hollow portion may be formed within the outside body 111, and a second opening part may be formed on one side of the hollow portion.

In this case, in an embodiment of the present invention, the inside body 113 may be coupled to the inside of the outside body 111 and rotated along with the outside body 111.

Referring to FIG. 9, in an embodiment of the present invention, the inside body 113 may be formed in a ring form, and the outer surface of the inside body may have an octagon form. In this case, the accommodation grooves 12 may be radially formed in the inside body 113 in a plural number.

Furthermore, in an embodiment of the present invention, the first support member 30 and the second support member 40 may be disposed in each of the plurality of accommodation grooves 12.

Figure 11:
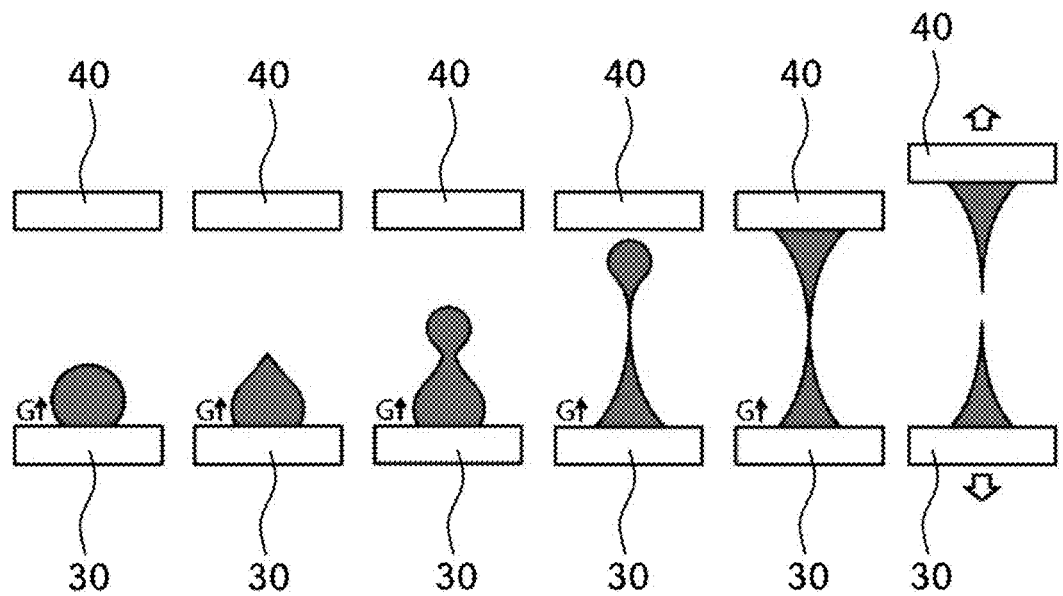
FIG. 11 is a schematic diagram showing that a viscous composition between the first support member and second support member of the rotation assembly according to an embodiment of the present invention is extended.

FIG. 11 is a schematic diagram showing that a viscous composition between the first support member and second support member of the rotation assembly according to an embodiment of the present invention is extended.

Referring to FIG. 11, in an embodiment of the present invention, the viscous composition G may be selected from a group consisting of hyaluronic acid and salt thereof, polyvinylpyrrolidone, cellulose polymer, dextran, gelatine, glycerine, polyethylene glycol, polysorbate, propylene glycol, povidone, carbomer, gum ghatti, guar gum, glucomannan, glucosamine, dammer resin, rennet casein, locust bean gum, microfibrillated cellulose, psyllium seed gum, xanthan gum, arabino galactan, arabic gum, alginic acid, gelatine, gellan gum, carrageenan, karaya gum, curdlan, keto acid, chitin, taragum, tamarind gum, tragacanth gum, furcelleran, pectin and pullulan, polystyrene, and polymer.

Hereinafter, the apparatus for fabricating a micro structure according to another embodiment of the present invention is described with reference to FIG. 12.

The apparatus 2 for fabricating a micro structure according to another embodiment of the present invention may include a housing 5, a rotation assembly 3, 100 positioned within the housing, a driving unit 8 and a pressure reduction unit 4 for reducing pressure within the housing 5.

Figure 12:
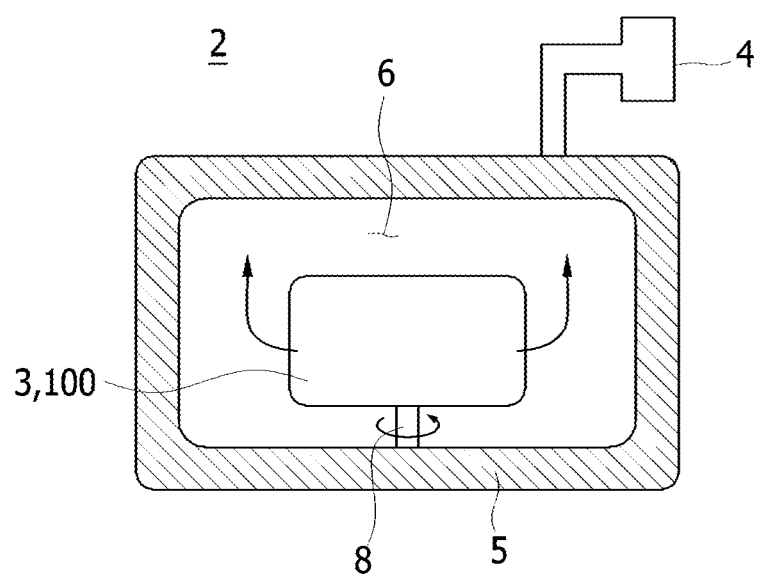
FIG. 12 is a diagram showing the operation of an apparatus for fabricating a micro structure according to another embodiment of the present invention.

As shown in FIG. 12, a hollow portion 6 is formed within the housing 5. The hollow portion may have relatively lower pressure than pressure outside the housing 5 or may be preferably formed in a vacuum and may be connected to the pressure reduction unit 4 for reducing pressure within the housing 5.

In this case, the rotation assembly 3, 100 is positioned within the housing and may be rotated by the driving unit 8.

A viscous composition may be positioned within the rotation assembly 3, 100. A fluid may communicate with the inside of the rotation assembly 3, 100 and the inside of the housing through a fluid communication unit. Furthermore, as described above, the fluid communication unit may be configured in various forms through which the inside of the rotation assembly 3, 100 and the inside of the housing 5 communicate with each other, such as a flow hole, a pipe part or isolation between parts of the rotation assembly 3, 100.

A detailed configuration of the rotation assembly 3, 100 has been described above, and thus a detailed description thereof is omitted.

The pressure reduction unit 4 may be positioned outside the housing 5 and can reduce pressure within the housing 5 by sucking a fluid within the housing 5. The pressure reduction unit 4 may include a vacuum pump.

The apparatus 2 for fabricating a micro structure according to another embodiment of the present invention can reduce pressure within the housing through the pressure reduction unit 4. When pressure within the housing is reduced, a viscous composition is evaporated from the rotation assembly 3, 100 and discharged to the outside of the rotation assembly 3, 100, that is, the inside of the housing. In this case, pressure within the housing may be reduced after the rotation of the rotation assembly 3, 100 is started, or the rotation of the rotation assembly 3, 100 and a reduction in pressure within the housing may be performed at the same time. Furthermore, after the rotation is stopped, pressure within the housing may be reduced.

In this case, the evaporated viscous composition may be discharged into the housing 5 through the fluid communication unit. As the viscous composition is evaporated, it is hardened within the rotation assembly 3, 100. As a result, a micro structure may be formed within the rotation assembly 3, 100.

The apparatus 2 for fabricating a micro structure according to another embodiment of the present invention can accelerate the hardening of a viscous composition extended within the rotation assembly 3, 100 by reducing pressure within the housing 5 outside the rotation assembly 3, 100. At this time, micro structures of various forms may be fabricated by differently forming pressure within the housing 5.

The apparatus 2 for fabricating a micro structure according to another embodiment of the present invention can form pressure within the housing 5 in various ways through the pressure reduction unit 4 and can harden a viscous composition.

In this case, the viscous composition may be evaporated by rapidly rotating the rotation assembly 3, 100 as in an embodiment of the present invention. However, another embodiment of the present invention has an effect in that a viscous composition can be evaporated using external differential pressure within the rotation assembly 3, 100 in addition to evaporation according to rotation.

In particular, there is an advantage in that a viscous composition within the rotation assembly 3, 100 can be hardened even without rotating the rotation assembly 3, 100. The rotation speed of the rotation assembly 3, 100 is related to the evaporation speed of a viscous composition, but may be closely related to a shape of a micro structure. In such a case, there are advantageous effects in that the shape of the micro structure can be adjusted by controlling the rotation speed and the hardening speed of the viscous composition can be adjusted by controlling pressure within the housing.

When the rotation assembly 3, 100 according to an embodiment of the present invention is rotated, the viscous composition G positioned in the first support member 30 is extended from a water-drop shape up to the inner surface of the second support member 40. A micro structure can be fabricated by cutting a portion formed in the middle portion of the extended viscous composition.

The rotation assembly and the apparatus for fabricating a micro structure including the same according to the embodiments of the present invention can fabricate a micro structure having a diameter of a micro unit and a sufficient effective length and hardness through a viscous composition using a centrifugal force.

The rotation assembly and the apparatus for fabricating a micro structure including the same according to the embodiments of the present invention can exclude a process that may break the activation of medication or a beauty ingredient, such as high temperature processing and organic solvent processing, reduce damage attributable to contact and separation, and overcome the limitation of an aspect ratio of a fabricated micro structure using a centrifugal force.

The rotation assembly and the apparatus for fabricating a micro structure including the same according to the embodiments of the present invention can minimize air resistance when the first support member and the second support member are rotated because the first support member and the second support member are disposed within the rotation body.

The rotation assembly and the apparatus for fabricating a micro structure including the same according to the embodiments of the present invention can adjust the time taken for the viscous composition G to be hardened based on the amount of an inflow or outflow fluid when the viscous composition is hardened because the flow hole is included.

The rotation assembly according to an embodiment of the present invention can prevent the first support member and the second support member from breaking away when they are rotated because the cover member is included, and can adjust the time taken for a viscous composition to be hardened by controlling the amount of an inflow fluid.

In the rotation assembly according to an embodiment of the present invention, since the handle groove is formed in the fixing member, the first support member and the second support member can be easily inserted and disposed.

The rotation assembly according to an embodiment of the present invention includes the guidance member, and thus can guide the fixing member when the fixing member is inserted into the accommodation groove.

The rotation assembly according to an embodiment of the present invention includes the interval maintenance member to maintain the interval between the first support member and the second support member. Accordingly, a viscous composition positioned on the outer surface of the first support member can be extended up to the inner surface of the second support member when the rotation body is rotated, thereby forming a micro structure.

The rotation assembly and the apparatus for fabricating a micro structure including the same according to the embodiments of the present invention can overcome a loss occurring in a cutting process when a viscous composition extended to the second support member is cut and the limitation of a fabrication yield because the holder member is included and the first support member and the second support member are separately separated.

The rotation assembly and the apparatus for fabricating a micro structure including the same according to the embodiments of the present invention can increase the yield of a micro structure in a single process because the plurality of coupling members is included.

The embodiments of the present invention have been described above, but the spirit of the present invention is not limited to the embodiments proposed in this specification and a person who understands the spirit of the present invention may readily propose other embodiments based on the addition, change, deletion or supplement of an element within the range of the same spirit. Such embodiments may be said to fall within the spirit of the present invention.

The invention claimed is:

1. A rotation assembly for forming a micro structure, comprising:
    a rotation body rotatable around an axis of a rotation shaft;
    a first support member positioned in the rotation body in such a way as to be apart from the rotation shaft, and configured to allow a viscous composition to be positioned on an outer surface of the first support member, the outer surface facing away from the rotation shaft;
    a second support member having an inner surface facing the outer surface of the first support member and spaced apart from the first support member in a radial direction perpendicular to the axis of the rotation shaft;
    an interval maintenance member positioned between the first support member and the second support member to maintain an interval between the first support member and the second support member;
    a fluid communication unit through which an inside of the rotation body is in communication with an outside of the rotation body; and
    an accommodation groove formed on an upper side of the rotation body, wherein the first support member and the second support member are disposed in the accommodation groove,
    wherein the first support member, the second support member, and the fluid communication unit are arranged in the rotation body such that, when the rotation body is rotated with the viscous composition positioned on the outer surface of the first support member, the rotation of the rotation body is configured to:
        cause a portion of the viscous composition to be extended outward in the radial direction up to the inner surface of the second support member, and
        cause a portion of the viscous composition is evaporated and discharged to the outside of the rotation body through the fluid communication unit, and
        cause the portion of the viscous composition extended in the radial direction to be hardened and formed into a micro structure.

2. The rotation assembly of claim 1, wherein the fluid communication unit comprises a flow hole formed in an outer circumference surface of the rotation body.

3. The rotation assembly of claim 2, wherein the accommodation groove is configured to communicate with the flow hole.

4. The rotation assembly of claim 3, further comprising a fixing member configured to fix the first support member and the second support member to the accommodation groove, wherein a cross section of the fixing member is formed to correspond to a cross section of the accommodation groove so that the fixing member is inserted into the accommodation groove.

5. The rotation assembly of claim 4, wherein:
    a coupling groove outward depressed in the radial direction is formed on one side of the fixing member, and
    the first support member and the second support member are coupled to an inner surface of the coupling groove.

6. The rotation assembly of claim 5, wherein the fixing member comprises guidance members protruded toward one side of the rotation body on both end sides of the one side to guide the fixing member when the fixing member is inserted into the accommodation groove.

7. The rotation assembly of claim 4, wherein:
the fixing member further comprises a fastening member configured to fix the fixing member to the accommodation groove,
the fastening member is a bolt,
a through hole through which the bolt penetrates is formed in the fixing member, and
a coupling hole to which the bolt is coupled is formed in the outer circumference surface of the rotation body.

8. The rotation assembly of claim 4, wherein the fixing member has a cross section of "a ⊂ letter" form.

9. The rotation assembly of claim 1, wherein the interval maintenance member comprises an interval frame having one side come into contact with the first support member and the other side come into contact with the second support member.

10. The rotation assembly of claim 9, wherein the interval frame is a holder member having a fixing groove formed in one surface in order to fix the first support member and having an end of the fixing groove come into contact with another surface of the second support member.

11. The rotation assembly of claim 5, wherein:
the first support member and the second support member are formed in a plural number,
the coupling groove comprises a plurality of coupling members arranged in parallel from one side within the coupling groove toward an end of the coupling groove, and
the plurality of first support members and the plurality of second support members are disposed in the plurality of coupling members.

12. The rotation assembly of claim 11, wherein:
each of the plurality of coupling members is formed in a sheet form, and
a protrusion member is protruded from one side of each of the plurality of coupling members to maintain an interval between the plurality of coupling members.

13. The rotation assembly of claim 12, wherein:
the accommodation groove is formed in a plural number in the radial direction of the rotation body, and
at least one of the first support member and the second support member is positioned in each of the plurality of accommodation grooves.

14. The rotation assembly of claim 13, wherein the first support member and the second support member are formed in a sheet or curve form.

15. The rotation assembly of claim 1, wherein the viscous composition is selected from a group consisting of hyaluronic acid and salt thereof, polyvinylpyrrolidone, cellulose polymer, dextran, gelatine, glycerine, polyethylene glycol, polysorbate, propylene glycol, povidone, carbomer, gum ghatti, guar gum, glucomannan, glucosamine, dammer resin, rennet casein, locust bean gum, microfibrillated cellulose, *psyllium* seed gum, xanthan gum, arabino galactan, arabic gum, alginic acid, gelatine, gellan gum, carrageenan, karaya gum, curdlan, keto acid, chitin, taragum, tamarind gum, tragacanth gum, furcelleran, pectin and pullulan, polystyrene, polymer.

16. The rotation assembly of claim 1, wherein after the rotation body is rotated, the first support member and the second support member are rotated to change their positions and are then rotated.

17. An apparatus for fabricating a micro structure, comprising:
a housing in which a hollow portion is formed;
a rotation assembly according to claim 1, wherein the rotation assembly is formed within the housing to rotate around an axis of a rotation shaft; and
a pressure reduction unit configured to reduce pressure of the hollow portion.

18. The apparatus of claim 17, further comprising a housing cover coupled to the housing to open or close an opening part formed on one side of the hollow portion.

19. The apparatus of claim 17, wherein the pressure reduction unit is configured to form a vacuum in the hollow portion.

20. The apparatus of claim 17, wherein a temperature and magnetic field of the hollow portion are adjustable.

* * * * *